United States Patent [19]
Kanojia

[11] 3,983,112
[45] Sept. 28, 1976

[54] 17β-ETHYNYL-3,17α-ESTRADIOL AND DERIVATIVES THEREOF

[75] Inventor: Ramesh Maganlal Kanojia, Somerville, N.J.

[73] Assignee: Ortho Pharmaceutical Corporation, Raritan, N.J.

[22] Filed: Sept. 4, 1973

[21] Appl. No.: 393,873

[52] U.S. Cl.................. 260/239.55 R; 260/397.4; 260/397.5; 424/243
[51] Int. Cl.$^2$............................................ C07J 1/00
[58] Field of Search ...................................
/Machine Searched Steroids

[56] References Cited
OTHER PUBLICATIONS
Engelfried et al. — *Arzneimittel Forschung*, vol. 16, pp. 1518–1521 (1966).

Rodds — *Chemistry of Carbon Compounds*, vol. II, Part D, 2nd Ed. (1970), pp. 304 & 307.

*Primary Examiner*—Elbert L. Roberts
*Attorney, Agent, or Firm*—Benjamin F. Lambert

[57] ABSTRACT

17β-ethynyl-3,17α-estradiol and derivatives thereof are prepared by epimerization of 17-acyl esters of 17α-ethynyl-3,17β-estradiol 3-ethers. 17β-ethynyl-3,17α-estradiol and its derivatives are active as post-coital antifertility agents and inhibit the growth of or reduce the size of the prostate gland and the seminal vesicle.

7 Claims, No Drawings

17β-ETHYNYL-3,17α-ESTRADIOL AND DERIVATIVES THEREOF

BACKGROUND OF THE INVENTION

Ethynylation of 17-keto steroids having a normal configuration at $C_{14}$ generally proceeds by attack of the reagent at the sterically less hindered α-side of the keto group which results almost exclusively in the production of the 17α-ethynyl-17β-ol derivative. Steroidal products resulting from attack at the 17β-side of the keto group have been reported, but the yields of these compounds generally have been very low. By means of the present invention, a novel process for the preparation of 17β-ethynyl-3,17α-estradiol and derivatives thereof is provided.

DESCRIPTION OF THE PREFERRED EMBODIMENTS

This invention relates to 17β-ethynyl-3,17α-estradiol and derivatives thereof. The novel compounds are 19-norpregna-1,3,5(10)-trien-20-yn-3,17α-diols and derivatives thereof and can be represented by the general formula:

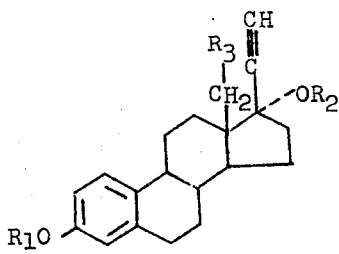

I wherein $R_1$ is hydrogen, lower alkyl of from 1 to 5 carbon atoms such as, for example, methyl, ethyl, propyl, butyl, isopropyl, pentyl, and the like; cycloalkyl having 4 to 6 carbon atoms such as, for example, cyclobutyl, cyclopentyl and cyclohexyl, and a lower acyl group having 2 to 6 carbon atoms such as, for example, acetyl, propionyl, butyryl, valeryl and the like;

$R_2$ is hydrogen or a lower acyl group having 2 to 6 carbon atoms, and $R_3$ is hydrogen or a lower alkyl group of from 1 to 2 carbon atoms. Preferred among the above compounds are those compounds wherein $R_1$ is hydrogen or lower alkyl, $R_2$ is hydrogen or lower acyl, and $R_3$ is hydrogen.

In general, the compounds of the present invention possess very low estrogenicity, but are nevertheless physiologically active agents. They exhibit preimplantive antifertility activity and also reduce the size of the prostate gland and the seminal vesicle.

The novel 17β-ethynyl-3,17α-estradiol [i.e., 19-norpregna-1,3,5(10)-trien-3,17α-diol] and its derivatives can be prepared by epimerization of 17-acyl esters of 17α-ethynyl-17β-diol 3-ethers [i.e., 17-acyl esters of 17α-pregna-1,3,5(10)-trien-20-yn-3,17β-diol 3-ethers] (Formula II) on activated alumina:

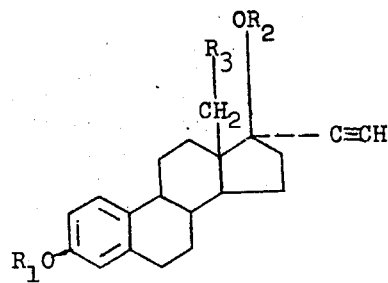

II wherein $R_1$ is lower alkyl or cycloalkyl; $R_2$ is acyl and $R_3$ is hydrogen or lower alkyl. A solution of a 17α-ethynyl-3,17β-diol 17-acyl ester 3-ether of Formula II is treated with activated alumina to effect epimerization. Generally, a nonpolar solvent such as benzene, toluene, carbon tetrachloride, tetrahydrofuran, and the like, is employed as the solvent. The reaction is carried out with activated alumina, having an activity of about 1, for several days. It is preferred to carry out the reaction for from about 2 to 10 days. Neutral, basic or acidic alumina may be employed, but it is preferred to carry out the reaction with neutral or basic alumina. The reaction can be carried out a temperature between about room temperature and 80°C., but it is preferred to carry out the reaction at room temperature. Generally, a ratio of alumina to steroid ranging from 1:100 to 1:20 is employed. The reaction can be carried out by allowing the solution of the steroid to sit on a column of alumina or the solution can be agitated with a slurry of alumina in a suitable reaction vessel. When the treated mixture is eluted with solvents of increasing polarity, e.g., increasing proportions of ethyl acetate in benzene, a mixture of products is obtained which includes (a) a $\Delta^{16}$-enyne (Formula III),

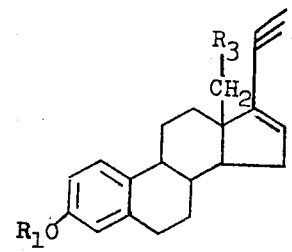

III (b) the starting 17-acyl derivative; (c) a mixture of the epimerized product, i.e., 17β-ethynyl-17α-ol of Formula I and an unsaturated aldehyde (Formula IV),

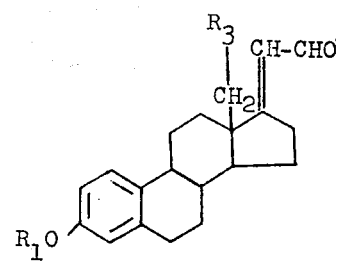

IV and (d) a 17α-ethynyl-17β-ol of Formula II wherein $R_1$ and $R_3$ are as previously defined.

The mixture of the 17β-ethynyl-17α-ol and the aldehyde can be separated either by chromatography followed by fractional crystallization or by removing the aldehyde through formation of a suitable Schiff base such as a semi-carbazone, for example.

The epimerized product of Formula I is generally obtained as an ether depending upon the particular starting material employed. The 3-ol compounds, i.e., those compounds wherein $R_1$ is hydrogen can be prepared by removal of the ether function. De-etherification can be carried out under neutral, basic or mildly acidic conditions. For example, the methyl ether ($R_1$ is $CH_3$) can be treated with a suitable demethylating agent such as diphenyl phosphide or arsenide anion, a lithium halide or an alkyl Grignard reagent. The preferred demethylating agent is an alkyl Grignard reagent of the type $RM_gX$, wherein R is a lower alkyl group of 1 to 5 carbon atoms and X is chlorine, iodine or bromine. Best results are obtained where methyl magnesium iodide is employed as the demethylation agent.

duction can be effected by employing any of the general epoxide reducing methods known in the art. It is preferred, however, to carry out the reaction with a metal hydride such as lithium aluminum hydride, for example. In the epoxide reduction method the 3-acyl substituted epoxides yield 17β-ethynyl-3,17α-estradiol directly whereas the 3-ether derivatives of the epoxide yield the corresponding 3-ethers of 17β-ethynyl-3,17α-estradiol which can be converted to 17β-ethynyl-3,17α-estradiol by removal of the 3-ether function.

The 17β-ethynyl-3,17α-epoxides of Formula V are in turn prepared by the epoxidation of the corresponding $\Delta^{16}$-enynes with a suitable per acid such as meta-chloroperbenzoic acid for example, according to the following reaction scheme:

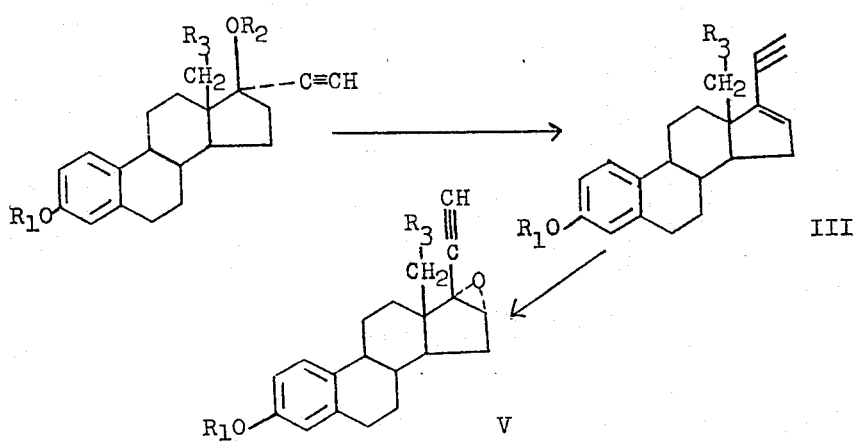

The reaction is generally carried out for several hours at a temperature between room temperature and about 190°C. Alternatively, the 3-ol compounds can also be prepared by treating the methyl ether with boron tribromide in a suitable solvent such as dichloromethane, for example, at a temperature of about −10°–0°C.

Conversely, the free 17β-ethynyl-3,17α-estradiol can be converted to various ethers by heating it with the appropriate alkyl or cycloalkyl halide, such as ethyl bromide, or cyclopentyl bromide and potassium carbonate in a suitable solvent such as methanol or ethanol. The various esters at $C_3$ and $C_{17}$ can also be prepared by heating the 17β-ethynyl-3,17α-estradiol with the anhydride of a lower aliphatic carboxylic acid such as acetic anhydride, for example.

In an alternate method 17β-ethynyl-3,17α-estradiol and its ethers can be obtained by the reductive opening of the corresponding 16α,17α-epoxy compound (Formula V),

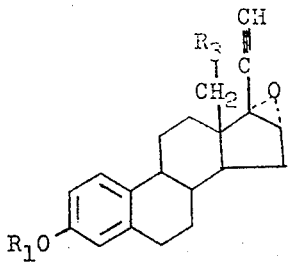

wherein $R_1$ and $R_3$ are as previously defined. The re-

The $\Delta^{16}$-enynes can be prepared by deacylation of 17α-ethynyl-3,17β-estradiol 3-ether, 17-acylate on alumina or by dehydration of 17α-ethynyl-3,17β-estradiol, 3-ether or the acyl derivative in pyridine with either phosphorous oxychloride or thionyl chloride.

The following examples illustrate the invention and are not to be construed as imposing any limitations thereon.

PREPARATION OF STARTING MATERIAL

Preparation A 3-methoxy-19-nor-17α-pregna-1,3,5(10)-trien-20-yn-17β-ol acetate A mixture of 3-methoxy-19-nor-17α-pregna-1,3,5(10)-trien-20-yn-17β-ol (10 g.) and acetic anhydride (200 ml.) is heated at reflux for 3 hours. The mixture is then cooled, poured into ice water (2,000 ml.) and stirred for several hours until the excess acetic anhydride is decomposed. The precipitate which forms is filtered, washed free from acid with water, and dried. Upon crystallization from methanol-ethyl acetate, 3-methoxy-19-nor-17α-pregna-1,3,5(10)-trien-20-yn-17β-ol acetate is obtained, m.p. 162°–163°C.

When in the above procedure 19-nor-17α-pregna-1,3,5(10)-trien-20-yn-3,17β-diol is employed in place of the corresponding 3-methoxy compound, 19-nor-17α-pregna-1,3,5(10)-trien-20-yn-3,17β-diol diacetate is obtained.

When in the above procedure propionic anhydride, butyric anhydride, or valeric anhydride is employed in place of acetic anhydride, the corresponding 17-acyl esters 3-ethers of 17α-ethynyl-3,17β-estradiol are obtained, e.g., 17α-ethynyl-3,17β-estradiol 3-methyl ether 17 propionate, 17α-ethynyl-3,17β-estradiol 3-methyl ether 17 butyrate, 17α-ethynyl-3,17β-estradiol 3-methyl ether 17-valerate respectively are obtained.

Preparation B 19-nor-17α-pregna-1,3,5(10)-trien-20-yn-3,17β-diol 17-acetate

A solution of 19-nor-17α-pregna-1,3,5(10)-trien-20-yn-3,17β-diol diacetate (5 g.) in methanol (300 ml.) is treated with a solution of potassium carbonate (2.5 g.) in water (20 ml.) and the resulting mixture is stirred at room temperature for 5 hours. The methanolic solution is then neutralized with dilute hydrochloric acid and evaporated to dryness under reduced pressure. The residue is extracted with chloroform and the chloroform layer is washed with water and dried over sodium sulfate. Upon removal of the solvent, a solid residue is obtained which is crystallized from benzene-hexane, m.p. 211°–212°C.

Preparation C 19-nor-17α-pregna-1,3,5(10)-trien-20-yn-3,17β-diol 3-acetate

A solution of 19-nor-17α-pregna-1,3,5(10)-trien-20-yn-3,17β-diol (1.0 g.) in pyridine (5 ml.) is treated at room temperature with acetic anhydride (2.5 ml.) for 1 hour. The reaction mixture is then poured into an ice-water mixture and extracted with ether. The ether layer is washed with water, dried over $Na_2SO_4$, and the solvent is removed under vacuum. The residue obtained is crystallized from benzene-hexane, to yield 19-nor-17α-pregna-1,3,5(10)-trien-20-yn-3,17β-diol 3-acetate, m.p. 152°–153°C.

When in the above procedure propionic anhydride, butyric anhydride or valeric anhydride is employed in place of acetic anhydride, the corresponding 3-acyl ester of 17α-ethynyl-3,17β-estradiol is obtained.

Preparation D 3-acetoxy-19-norpregna-1,3,5(10),16-tetraen-17-yne

A solution of 17α-ethynyl-3,17β-estradiol 3-acetate (4.5 g.) in dry pyridine (40 ml.) is treated with freshly distilled phosphorous oxychloride (2.45 ml.) and heated at reflux for 2 hours. The resulting mixture is then cooled and poured into ice water containing concentrated hydrochloric acid (50 ml.). The mixture is extracted with ether and the organic phase is washed with water, 10% sodium bicarbonate and water and then dried over $Na_2SO_4$. Upon evaporation of the solvent, 2.95 g. of a solid residue are obtained. Purification of the residue on a column of silica followed by recrystallization from methanol affords 3-acetoxy-19-norpregna-1,3,5(10),16-tetraen-17-yne, m.p. 114°–115°C.

When in the above procedure 17α-ethynyl-3,17β-diol 3-methyl ether is employed in place of 3-acetoxy-19-norpregna-1,3,5(10)-16-tetraen-17-yne the corresponding $\Delta^{16}$-enyne, 3-methoxy-19-norpregna-1,3,5(10),16-tetraen-17-yne, m.p. 156°–157°C. is obtained.

EXAMPLE I 3-methoxy-19-norpregna-1,3,5(10)-trien-20-yn-17α-ol

A solution of 3-methoxy-19-norpregna-1,3,5(10)-trien-20-yn-17β-ol acetate (10 g.) in benzene (50 ml.) is allowed to sit on a column of neutral alumina (Woelm, grade I, activity 1; 1,000 g.) for 5 days. Upon elution with benzene containing increasing portions of ethyl acetate, a large number of fractions (125 ml. each) is collected. These are pooled into three major fractions on the basis of thin layer chromatography examination.

Fraction (i) 3.5 g., represents the fastest moving material consisting largely of 3-methoxy-17-pregna-1,3,5(10),16-tetraen-20-yn-3-ol.

Fraction (ii) consists of four components. The first one is 3-methoxy-19-nor-17α-pregna-1,3,5(10)-trien-20-yn-17β-ol acetate; the second one is the epimerized product: 3-methoxy-19-norpregna-1,3,5(10)-triene-20-yn-17α-ol; the third one is 3-methoxy-19-norpregna-1,3,5(10), 17(20)-tetraen-21-al; and the fourth one is 3-methoxy-19-nor-17α-pregna-1,3,5(10)-trien-20-yn-17β-ol.

Fraction (iii) is mainly 3-methoxy-19-nor-17α-pregna-1,3,5(10)-trien-20-yn-17β-ol.

Careful rechromatography of fraction (ii) on silicic acid with ethyl acetate in benzene affords 3-methoxy-19-norpregna-1,3,5(10)-trien-20-yn-17α-ol in 5% yield. Upon recrystallization from methanol, a product having m.p. 136°–137°C., $(\alpha)_D^{24} + 71.8$ (C, 1.0 $CHCl_3$) is obtained.

EXAMPLE II 19-norpregna-1,3,5(10)-trien-20-yn-3,17α-diol

In a three-necked, 2 liter round bottomed flask equipped with a magnetic stirrer, a gas inlet tube and an air condenser, is charged an ethereal solution of methyl magnesium iodide (2.6 molar, 278 ml.) followed by 3-methoxy-19-norpregna-1,3,5(10)-trien-20-yn-17α-ol (11.8 g.) under an atmosphere of argon. The mixture is heated slowly in an oil bath to 175°C. and maintained at that temperature for an additional 3 hours. The flask is then cooled in a dry ice-acetone bath. A mechanical stirrer is introduced to break up the solidified foamy mass in the flask and a saturated solution of $NH_4Cl$ (500 ml.) is added carefully (highly exothermic). The mixture is adjusted to pH 5 and extracted with ethyl acetate. The ethyl acetate layer is washed with water, dried over $Na_2SO_4$, and a crystalline residue (16 g.) is obtained upon removal of the solvent. The residue is chromatographed on a column of neutral silica (800 g.) and eluted with 3 to 5% ethyl acetate in benzene to afford 10.0 g. of solid material. Decolorization with charcoal and recrystallization from acetone-hexane yields 7.9 g. of 19-norpregna-1,3,5(10)-trien-20-yn-3,17α-diol, m.p. 210°–212°C., $(\alpha 0_D^{25} + 68$°C. (C, 1.0, dioxane).

EXAMPLE III 3-methoxy-19-norpregna-1,3,5(10)-trien-20-yn-17α-ol

Lithium aluminum hydride (10 g.) is added to a solution of 3-methoxy-16α,17α-epoxy-19-norpregna-1,3,5(10)-trien-20-yne (10 g.) in tetrahydrofuran (800 ml.) and the resulting mixture is stirred and heated at reflux for 1.5 hours under nitrogen. The mixture is cooled in an ice-bath, and to it, in succession, water (10 ml.), 15% NaOH solution (10 ml.) and again water (30 ml.) are added very carefully with vigorous stirring. The granular precipitate of aluminum oxides is removed by filtration and washed several times with ether. The combined tetrahydrofuran and ether solutions are evaporated to dryness. The residue is chromatographed on neutral silica (500 g.) and eluted with increasing proportions of ethyl acetate in benzene. The first product to come out of the column is 17-pregna-1,3,5(10), 16-tetraen-20-yn-3-ol methyl ether; the second one is 3-methoxy-19-norpregna-1,3,5(10)-trien-20-yn-17α-ol; and the remainder is a mixture of two epimeric 17-ethynyl-16-ols.

Recrystallization of 3-methoxy-19-norpregna-1,3,5(10)-trien-20-yn-17α-ol from methanol affords a product having m.p. 136°–137°C., which is identical with that obtained by the epimerization procedure described in Example I.

EXAMPLE IV 3-cyclopentoxy-19-norpregna-1,3,5(10)-trien-20-yn-17α-ol

A solution of 19-norpregna-1,3,5(10)-trien-20-yn-3,17α-diol (6.0 g.) in ethanol (200 ml.) is added to a suspension of $K_2CO_3$ (8.0 g.) in cyclopentyl bromide (12 g.) and the resultant mixture is heated to reflux under nitrogen for 4 hours. The reaction mixture is then cooled; the solvent is removed under reduced pressure, and the residue is partitioned between water and ether. The organic layer is washed, dried over $Na_2SO_4$ and the ether is removed under vacuum. The glassy residue is purified by chromatography on neutral silica (400 g.). Elution with 0.5% ethyl acetate in benzene affords 6.0 g. of solid material. Upon recrystallization from methanol, 3-cyclopentoxy-19-norpregna-1,3,5(10)-trien-20-yn-17α-ol, m.p. 113°–114°C., $(\alpha)_D^{26}$ + 62.5°C. (C, 1.0, $CHCl_3$) is obtained.

EXAMPLE V 3-methoxy-16α-17α-epoxy-19-norpregna-1,3,5(10)-trien-20-yne

To a solution of 3-methoxypregna-1,3,5(10),16-tetra-en-17-yne (5.5 g.) in chloroform (250 ml.) at room temperature is added with stirring a solution of m-chloroperbenzoic acid (8.0 g.) in chloroform (300 ml.) over a period of 30 minutes. The stirring is continued for an additional 5 hours after which a solution of $NaHSO_3$ (10%) is added to destroy the excess peracid. The chloroform solution is then washed successively with a solution of sodium bicarbonate (10%, 3×250 ml.) and water. After drying over sodium sulfate, the chloroform is removed by distillation and the residue chromatographed on neutral silica gel. Upon elution with benzene-petroleum ether (35:65) unreacted-enyne is obtained. Elution with benzene-petroleum ether (50:50) affords the epoxide (2.85 g.). Upon recrystallization from methylene chloride-methanol a sample having m.p. 199.5°C., $(\alpha_D^{26}$ + 103°C. (C, 0.5, $CHCl_3$) is obtained.

EXAMPLE VI 3,17α-diacetoxy-19-norpregna-1,3,5(10)-trien-20-yne

When the procedure of Preparation A is employed using 19-norpregna-1,3,5(10)-trien-20-yn-3,17α-diol as the starting material, 3,17α-diacetoxy-19-norpregna-1,3,5(10)-trien-20-yne, m.p. 205°–208°C. (d), $(\alpha)_D^{24}$ + 47°C. (C, 0.9, $CHCl_3$) is obtained.

When in the above procedure 3-methoxy-19-norpregna-1,3,5(10)-trien-20-yn-3,17α-diol is employed in place of the corresponding 3-methoxy compound, 3-methoxy-19-norpregna-1,3,5(10)-trien-20-yn-17α-ol acetate is obtained.

When in the above procedure propionic anhydride, butyric anhydride or valeric anhydride is employed in place of acetic anhydride, the corresponding 3,17-diacyl esters of 17β-ethynyl-3,17α-estradiol are obtained, e.g., 17β-ethynyl-3,17α-estradiol 3,17α-dipropionate, 17β-ethynyl-3,17α-estradiol-3,17α-dibutyrate, 17β-ethynyl-3,17α-estradiol-3,17α-divalerate respectively are obtained.

EXAMPLE VII 3-acetoxy-17α-hydroxy-19-norpregna-1,3,5(10)-trien-20-yne

When the procedure of Preparation C is employed using 19-norpregna-1,3,5(10)-trien-20-yn-3,17α-diol as the starting material, 3-acetoxy-17α-hydroxy-19-norpregna-1,3,5(10)-trien-20-yne, m.p. 131°–132°C., $(\alpha)_D^{24}$ + 64.2°C. (C, 1.0, $CHCl_3$) is obtained.

When in the above procedure propionic anhydride, butyric anhydride or valeric anhydride is employed in place of acetic anhydride, the corresponding 3,17α-diol 3-esters of 17β-ethynyl-3,17α-estradiol are obtained, e.g., 17β-ethynyl-3,17α-estradiol 3-propionate, 17β-ethynyl-3,17α-estradiol-3-butyrate, 17β-ethynyl-3,17α-estradiol-3-valerate respectively are obtained.

EXAMPLE VIII 19-norpregna-1,3,5(10)-trien-20-yn-3,17α-ol

When in the procedure of Example III, 3-acetoxy-16α,17α-epoxy-19-norpregna-1,3,5(10)-trien-20-yne is employed as the starting material, the product obtained is 19-norpregna-1,3,5(10)-trien-20-yn-3,17α-ol, m.p. 210°–212°C., which is identical with that obtained from Example II.

EXAMPLE IX 19-norpregna-1,3,5(10)-trien-20-yn-3,17α-diol

A solution of 3-methoxy-19-norpregna-1,3,5(10)-trien-20-yn-17α-ol (0.5 g.) in dichloromethane (25 ml.) is treated with stirring at −10°C. with boron tribromide (1.7 ml.) and the resulting solution is allowed to stir at −10°C. under nitrogen for 1.5 hours. The reaction mixture is then treated with water and the organic phase is washed with dilute $NaHCO_3$ solution and water and then dried over $Na_2SO_4$. The residue obtained upon removal of the solvent is chromatographed on silica and eluted with 3 to 5% ethyl acetate in benzene to afford a product having a m.p. of 210°–212°C., which is identical with the product obtained by the procedure described in Example II.

As indicated above, the novel 17β-ethynyl-17α-estradiols of this invention are useful as post-coital antifertility agents and inhibit the growth of or reduce the size of the prostate gland and the seminal vesicle.

In order to determine the preimplantive antilittering effect of a given compound, a female animal, such as a rat, mouse, or hamster, for example, is fed the compound to be tested. Adult female rats are smeared daily and at the period immediately preceding estrus (proestrus) they are caged overnight with male rats of proven fertility. On the following morning, the females are examined for the presence of sperm in their vaginal washings. The day on which sperm are found constitutes the first day of pregnancy (Day 1). The rats are fed the test compound dissolved in sesame oil by gavage on day 1 through the sixth day of pregnancy and are sacrificed on the fourteenth day. The uterii are then examined for implantation and resorbtion sites. A control group is similarly treated except that the compound is not administered.

The results of the above test are shown in the following table for the noted compounds.

| Compound | Dose mg/kg | Animal | Day of Administration | Pregnant Total |
|---|---|---|---|---|
| 3-methoxy-17 α -hydroxy-19-norpregna-1,3,5(10)-trien-20-yne | 50mg. | Rat | 3 | 0/5 |
| 3-cyclopentoxy-17 α-hydroxy-19-norpregna-1,3,5(10)-trien-20-yne | 10 | Rat | 1–3 | 0/5 |
| | 10 | Rat | 4–6 | 0/5 |
| | 5 | Rat | 3 | 0/5 |
| | 1 | Rat | 3 | 3/5 |
| | 10 | Mouse | 1–6 | 0/11 |
| | 10 | Hamster | 1–6 | 4/7 |

In order to determine the prostate reducing activity mature male rats of the Wistar strain, 180–200 g., are injected (S.C.) with the test drug daily for 3 weeks. At the end of this period, the total prostate and seminal vesicles are removed and weighed. Five rats are used for each dose group. Controls receive only the vehicle. Results are expressed as the percentage reduction induced by the test drug compared to the controls. This is calculated by dividing the mean weight of the tissue of animals dosed with the test drug by that of the controls.

An example of the prostate reducing activity of the novel steroids may be illustrated by studies carried out with 3,17α-dihydroxy-19-norpregna-1,3,5(10)-trien-20-yne. A careful examination of the organs of the sacrificed male rats indicates that treatment with 2–5 mg/kg will reduce the weight of the prostate gland by 20–42%. In addition, the weight of the seminal vesicle is reduced by 34–56%. As little as 0.5 mg/kg will reduce the weight of the prostate by 13.75% and the seminal vesicle by 11.8%.

The amount of a given compound to be employed in a given instance will depend on the species being tested. The specific dose and regimen utilized will depend not only on the species being treated, but also on the compound chosen. An effective dose for a particular species and compound can be readily determined by routine clinical and laboratory screen.

What is claimed is:

1. A compound of the formula:

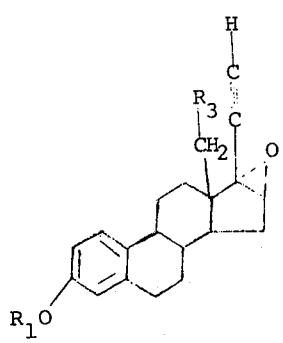

wherein $R_1$ is hydrogen, lower alkyl, cycloalkyl or lower acyl having 2–6 carbon atoms; $R_3$ is hydrogen.

2. The compound of claim 1 which compound is 3-acetoxy-16α,17α-epoxy-19-norpregna-1,3,5(10)-trien-20-yne.

3. The process for the preparation of a compound of claim 1 of the formula:

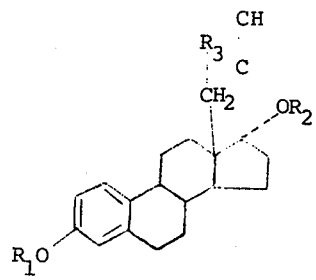

which comprises treating a compound of the formula:

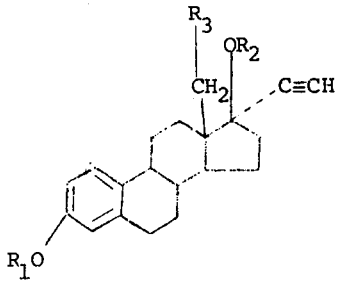

with alumina in a solvent, wherein $R_1$ hydrogen, lower alkyl, cycloalkyl or lower acyl having 2–6 carbon atoms, $R_2$ is hydrogen or lower acyl having 2–6 carbon atoms, and $R_3$ is hydrogen.

4. The process of claim 3 wherein the solvent is benzene.

5. The process of claim 3 wherein $R_1$ is hydrogen or lower alkyl, $R_2$ is hydrogen or lower acyl having 2–6 carbon atoms, and $R_3$ is hydrogen.

6. The process of claim 3 wherein $R_1$ is lower alkyl, $R_2$ is lower acyl having 2–6 carbon atoms, and $R_3$ is hydrogen.

7. The process of claim 3 wherein $R_1$ is lower acyl having 2–6 carbon atoms and $R_2$ and $R_3$ are hydrogen.

* * * * *

UNITED STATES PATENT AND TRADEMARK OFFICE
CERTIFICATE OF CORRECTION

PATENT NO. : 3,983,112
DATED : September 28, 1976
INVENTOR(S) : Ramesh Maganlal Kanojia Page 1 of 2

It is certified that error appears in the above-identified patent and that said Letters Patent are hereby corrected as shown below:

In Column 6, line 51, "$(\alpha 0)_D^{25}$" should read --- $(\alpha)_D^{25}$ ---.

In Column 9, Claim 1, the formula is unclear; it should read:

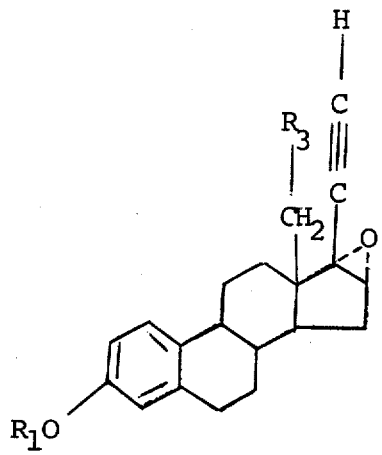

UNITED STATES PATENT AND TRADEMARK OFFICE
CERTIFICATE OF CORRECTION

PATENT NO. : 3,983,112
DATED : September 28, 1976

INVENTOR(S) : Ramesh Maganlal Kanojia

It is certified that error appears in the above-identified patent and that said Letters Patent are hereby corrected as shown below:

In Column 10, Claim 3, the first formula is unclear; it should read:

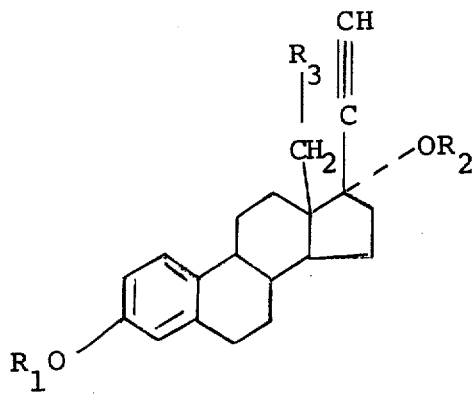

Signed and Sealed this

Tenth Day of May 1977

[SEAL]

Attest:

RUTH C. MASON
Attesting Officer

C. MARSHALL DANN
Commissioner of Patents and Trademarks